United States Patent [19]
Matsuzaki et al.

[11] Patent Number: 5,451,748
[45] Date of Patent: Sep. 19, 1995

[54] CERAMIC HEATER FOR OXYGEN SENSOR OF THE TYPE HAVING OXYGEN ION CONDUCTIVE TUBE OF SOLID ELECTROLYTE

[75] Inventors: Hiroshi Matsuzaki; Yoshiaki Kuroki; Takao Kojima, all of Nagoya, Japan

[73] Assignee: NGK Spark Plug Co., Ltd., Nagoya, Japan

[21] Appl. No.: 278,958

[22] Filed: Jul. 22, 1994

[30] Foreign Application Priority Data

Jul. 23, 1993 [JP]  Japan .................. 5-202774

[51] Int. Cl.⁶ .................. H05B 3/44; H05B 3/48
[52] U.S. Cl. .................. 219/543; 219/544; 219/553; 338/34; 338/307; 338/308; 338/309
[58] Field of Search .................. 219/553, 543, 544; 338/307, 308, 34, 309

[56] References Cited

U.S. PATENT DOCUMENTS

| | | | |
|---|---|---|---|
| 4,414,531 | 11/1983 | Novak .................. | 338/34 |
| 4,507,191 | 3/1985 | Ebizawa et al. .................. | 219/543 |
| 4,528,086 | 7/1985 | Kato et al. .................. | 219/541 |
| 4,591,423 | 5/1986 | Kato et al. .................. | 338/34 |
| 4,656,863 | 4/1987 | Takami et al. .................. | 338/34 |
| 4,660,407 | 4/1987 | Takami et al. .................. | 338/34 |
| 4,697,165 | 9/1987 | Ishiguro et al. .................. | 338/34 |
| 4,883,947 | 11/1989 | Murase et al. .................. | 219/553 |
| 5,264,181 | 11/1993 | Nozaki et al. .................. | 219/544 |

FOREIGN PATENT DOCUMENTS

59-0913579  5/1984  Japan .

*Primary Examiner*—Bruce A. Reynolds
*Assistant Examiner*—Sang Y. Paik
*Attorney, Agent, or Firm*—Foley & Lardner

[57] ABSTRACT

In an oxygen sensor of the type having an oxygen ion conductive tube of solid electrolyte, a ceramic heater disposed within the oxygen ion conductive tube for heating the same is in the form of a quadrangular prism or a bar of a rectangular cross section. The ceramic heater is formed by piling up ceramic green sheets with metallic thick-film patterns for heat generating resistors interposed between adjacent two of the ceramic green sheets. The ceramic heater is so shaped as to satisfy the relation of $b/a = 0.75 \sim 1$ where "a" is the width and "b" is the thickness of the ceramic heater. The metallic thick films, which the metallic thick-film patterns are turned to by firing, are arranged so as to be parallel to the side surfaces opposed in the thickness direction of the ceramic heater.

12 Claims, 6 Drawing Sheets b/a=77% b/a=100%

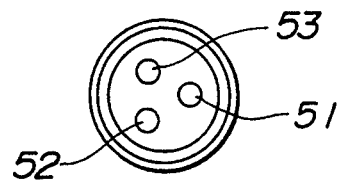
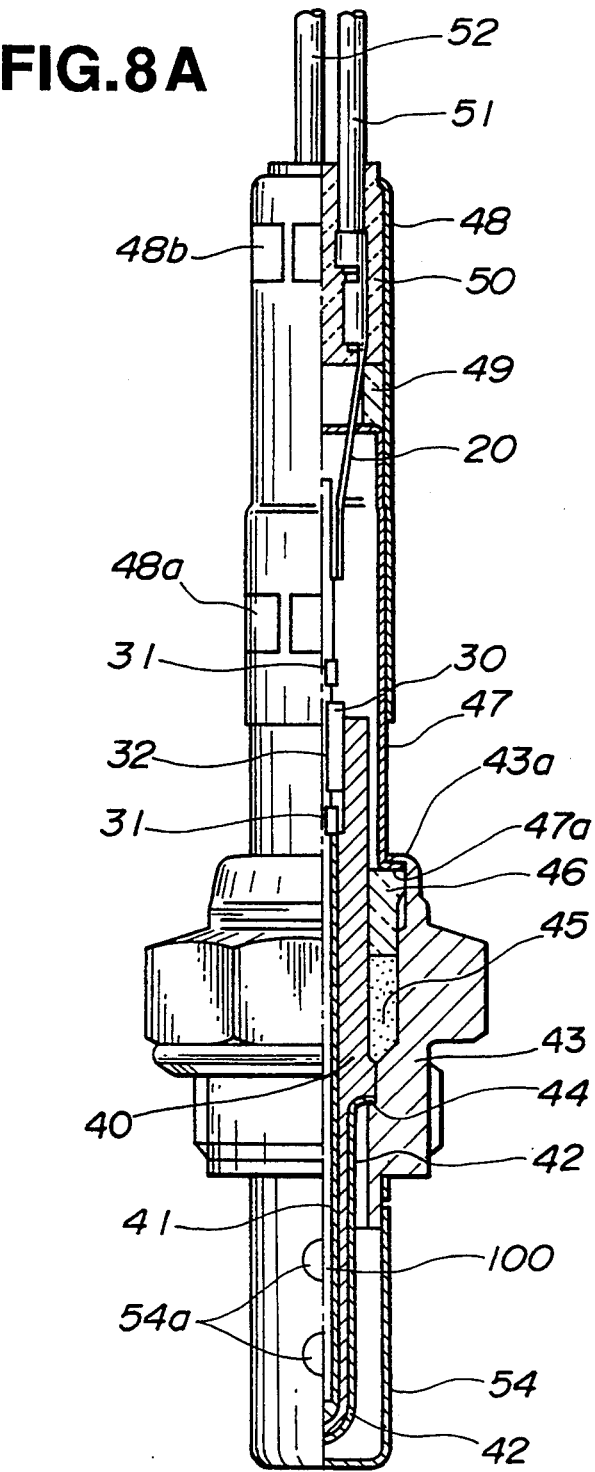

CERAMIC HEATER FOR OXYGEN SENSOR OF THE TYPE HAVING OXYGEN ION CONDUCTIVE TUBE OF SOLID ELECTROLYTE

BACKGROUND OF THE INVENTION

1. Field of the Invention

The present invention relates in general to oxygen sensors and more particularly to a ceramic heater for use in an oxygen sensor of the type having an oxygen ion conductive tube of solid electrolyte. The present invention further relates to a method of producing a ceramic heater for such an oxygen sensor.

2. Description of the Prior Art

An example of a ceramic heater for use in an oxygen sensor of the type described above is disclosed in Japanese Patent Provisional Publication No. 59-91357. The ceramic heater is an alumina ceramic heater and in the form of a round, straight bar correspondingly to the inner circumferential surface of the solid electrolyte tube.

Advantages of the ceramic heater in the form of a round, straight bar are that it has a heat generating surface in the vicinity of the inner circumferential surface of the oxygen ion conductive tube of solid electrolyte and capable of heating the solid electrolyte tube substantially uniformly, that its transverse rupture strength is substantially uniform with respect to any transverse direction, and that it is shaped so as to have a less possibility of causing a concentrated thermal stress.

However, as shown in FIGS. 9A and 9B, the ceramic heater of this kind is produced by preparing a prefired, hollow cylindrical ceramic core 201, placing around the ceramic core 201 a ceramic green sheet 202 on which a high melting point metallic thick-film pattern 203 for a heat generating resistor is previously printed, then bonding the green sheet 202 to the ceramic tube 201 by application of force, and cofiring the ceramic tube 201 and the green sheet 202 and allowing them to be turned into a ceramic heater 200. A disadvantage of the prior art bar ceramic heater is a high cost since the ceramic core requires a prefiring process, the process for winding the ceramic green sheet on the ceramic core requires a number of steps or particular and expensive devices, and a process for bonding the ceramic green sheet to the ceramic core by application Of force requires an expensive machine such as a rubber press. Another disadvantage is that it is difficult to carry out the above described winding and bonding of the ceramic green sheet precisely as desired and therefore peeling off of the ceramic sheet wound on the core may possibly be caused.

SUMMARY OF THE INVENTION

According to an aspect of the present invention, there is provided a ceramic heater for an oxygen sensor of the type having an oxygen ion conductive tube of solid electrolyte with an end closed. The ceramic heater comprises a ceramic heater main body in the form of a quadrangular prism of the width "a" and the thickness "b" and so shaped that the ratio of the thickness "b" to the width "a" is in the range from 0.75 to 1, and at least two metallic thick-films for heat generating resistors embedded in the ceramic heater main body in parallel to side surfaces of the ceramic heater main body opposed in the thickness direction. In the foregoing, it is to be noted that the term "thickness" is intended to indicate the overall thickness including bending and warping but simply referred to so herein for brevity.

According to another aspect of the present invention, a ceramic heater comprises a ceramic heater main body in the form of a bar of a rectangular cross section and so shaped as to satisfy b/a=0.75~1 where "a" is the width of the ceramic main body and "b" is the thickness of the ceramic main body, and a plurality of metallic thick-films for heat generating resistors embedded in the ceramic heater main body in parallel to side surfaces of the ceramic heater main body opposed in the thickness direction. The metallic thick-films are constructed and arranged so as to generate a less amount of heat at or adjacent to side surfaces of the ceramic heater main body opposed in the width direction and a larger amount of heat at or adjacent to the side surfaces of the ceramic heater main body opposed in the thickness direction.

According to a further aspect of the present invention, there is provided an oxygen sensor which comprises an oxygen ion conductive tube of solid electrolyte and having an end closed, and a ceramic heater disposed within said oxygen ion conductive tube for heating the same, wherein the ceramic heater includes a ceramic heater main body in the form of a quadrangular prism and so shaped as to satisfy the relation of b/a=0.75~1 where "a" is the width of the ceramic main body and "b" is the thickness of the ceramic main body, and a plurality of metallic thick-films for heat generating resistors embedded in the ceramic heater main body in parallel to side surfaces of the ceramic heater main body opposed in the thickness direction.

According to a further aspect of the present invention, there is provided a method of producing a ceramic heater for an oxygen sensor of the type having an oxygen ion conductive tube of solid electrolyte. The method comprises the steps of laying two ceramic green sheets one upon another with a metallic thick-film pattern for a heat generating resistor interposed therebetween and bonding said green sheets by application of force to obtain a pile, laying two of the piles one upon another, bonding the piles by application of force to obtain a pile assembly and cutting the pile assembly to size in such a manner that the metallic thick films are parallel to side surfaces opposed in the thickness direction of the pile assembly having been cut to size, and firing the pile assembly having been cut to size.

According to a further aspect of the present invention, a method of producing a ceramic heater comprises the steps of preparing a ceramic green body in the form of a bar of a rectangular cross section, laying metallic thick-film patterns for heat generating resistors on side surfaces of the ceramic green body opposed in the thickness direction and firing the ceramic green body and the metallic thick-film patterns to obtain a sintered body formed with metallic thick-films on side surfaces thereof, and spraying a ceramic powder material on the side surfaces of the sintered body to form a fine surface layer covering ceramic thick films.

The above structures and methods are effective for solving the above noted problems inherent in the prior art oxygen sensor.

It is accordingly an object of the present invention to provide a novel and improved ceramic heater for an oxygen sensor of the type having an oxygen ion conductive tube with an end closed, which can be produced with ease and therefore at a reduced cost without deteriorating the efficiency.

It is another object of the present invention to provide a novel and improved ceramic heater of the above described character which has a good migration resisting property and a good durability.

It is a further object of the present invention to provide a novel and improved ceramic heater of the above described character which is stable in quality and therefore reliable in operation.

It is a further object of the present invention to provide a novel and improved ceramic heater of the above described character which has a high transverse rupture strength and is suited for disposition within the oxygen ion conductive tube of solid electrolyte.

BRIEF DESCRIPTION OF THE DRAWINGS

FIG. 1 is a graph of rated transverse rupture strength of ceramic heater for a ratio of b/a;

FIG. 8A is a side elevational, partly sectioned view of an oxygen sensor of the type having an oxygen ion conductive tube of solid electrolyte, incorporating a ceramic heater of the present invention;

FIG. 8B is a top plan view of the oxygen sensor of FIG. 8A; and

DETAILED DESCRIPTION OF THE PREFERRED EMBODIMENTS

Before describing the preferred embodiments in detail, important features of the invention will first be described briefly.

Heretofore, it has been practiced to utilize a ceramic heater in the form of a round, straight bar in an oxygen sensor of the type having an oxygen ion conductive tube with an end closed for the reason that it is believed to be essential for the ceramic heater of this kind to be round in cross section in order that the oxygen ion conductive tube of solid electrolyte is heated uniformly. An important feature of the present invention resides in the discovery that it is not essential for a ceramic heater for use in an oxygen sensor of the type described above to be in the form of a round bar but the ceramic heater of this kind can be in the form of a rectangular bar or a quadrangular prism without causing any substantial deterioration in the heating efficiency, i.e., an oxygen ion conductive tube of solid electrolyte can be heated with efficiency and without any problem by means of a ceramic heater in the form of a bar of a rectangular cross section.

Figure 1:
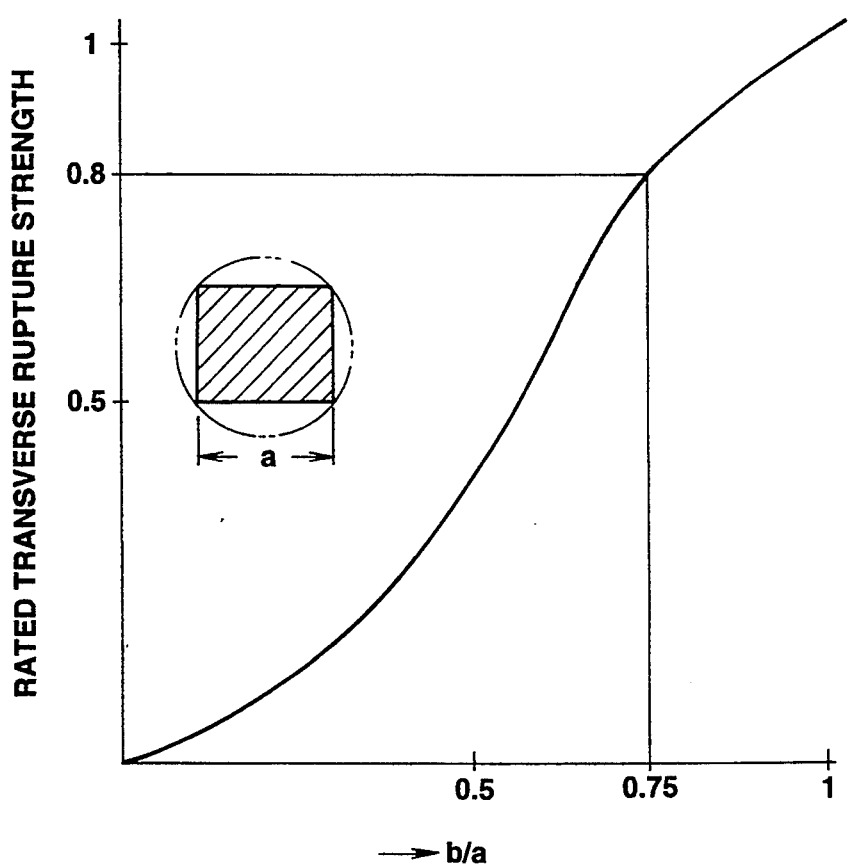

Another important feature of the present invention resides in the discovery that it is preferable for the ceramic heater in the form of a rectangular bar or quadrangular prism to be shaped so as to satisfy the relation of $b/a = 0.75 \sim 1$ where "a" is the width and "b" is the thickness of the ceramic heater in order that the inner surface of the oxygen ion conductive tube provided with a porous material electrode layer is not damaged by the ceramic heater at the time of installation and in use and further that the ceramic heater has a sufficient transverse rupture strength. More specifically, a ceramic heater for current oxygen sensors of the above described type needs to have the length equal to or larger than 50 mm so that it can be inserted into the oxygen ion conductive tube in a desired manner whilst being connected to electrode terminals through which it is energized. Due to this, bending and warping of the ceramic heater are apt to occur, thus causing a possibility of damaging the inner surface of the oxygen ion conductive tube at the time of installation and in use. By the experiments conducted by the applicant, it was revealed that the rectangular cross sectional shape of the ceramic heater that satisfies the relation of $b/a = 0.75 \sim 1$ is effective not only for preventing the bending and warping from becoming larger than a predetermined value but for preventing the transverse rupture strength from becoming smaller than a predetermined value. In this connection, FIG. 1 shows the relation between the rated rupture strength (i.e., the ratio of the transverse rupture strength of the ceramic heater in the rectangular bar to that of the ceramic heater in the form of a square bar) and the ratio of b/a of ceramic heater, which is obtained by the experiments conducted by the applicants. As seen from the graph of FIG. 1, the rated transverse rupture strength decreases relatively gradually as the ratio of b/a decreases in the range from 1 to 0.75. From this, it will be understood that it is preferable to set the ratio of b/a within the range from 0.75 to 1 in order that the transverse rupture strength of the ceramic heater is maintained at a relatively large value. In this connection, it is more preferable that the ratio of b/a is equal to or larger than 0.85 for obtaining a sufficiently large transverse rupture strength. By constructing the ceramic heater in such a manner as to satisfy the relation of $b/a = 0.75 \sim 1$, a variation of transverse rupture strength depending upon a variation of a transverse direction can be maintained smaller than a predetermined value.

A further important feature of the present invention resides in the discovery that it is preferable for the metallic thick-films for heat generating resistors embedded in the ceramic heater to be arranged in parallel to the side surfaces opposed in the thickness direction of the ceramic heater in order to prevent the bending and warping of the ceramic heater. In this connection, in order to prevent the bending and warping of the ceramic heater, it is also effective to form the ceramic heater from more than three ceramic green sheets which are laid one after another and constructing the ceramic heater so that the coefficient of contraction of the uppermost and lowermost layers at the time of firing are equal to or smaller than 1%.

Figure 2:
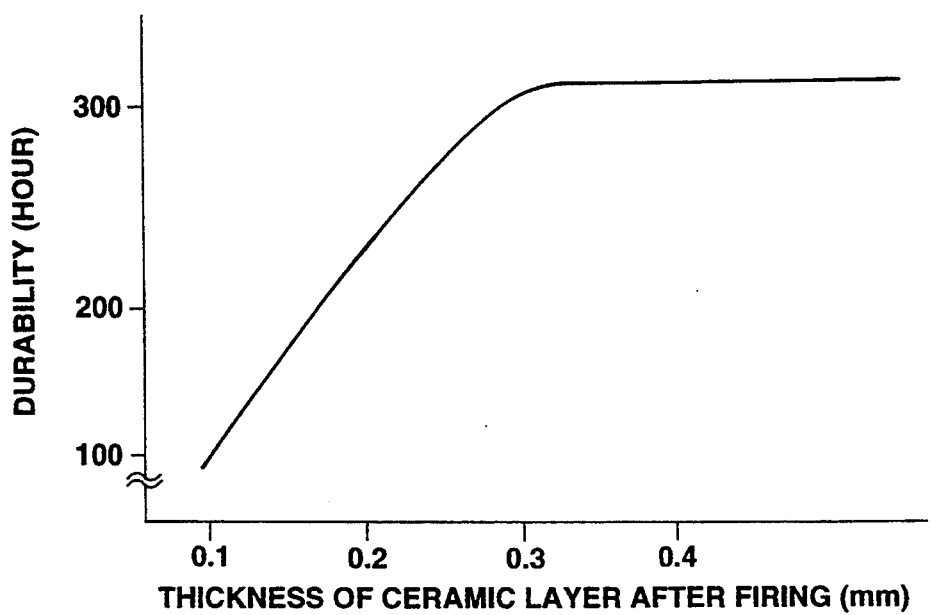
FIG. 2 is a graph of the relation between durability and thickness of ceramic layer.

A further important feature of the present invention resides in the discovery that a ceramic heater in the form of a rectangular bar or quadrangular prism is far more advantageous than that in the form of a round bar with respect to a migration resisting property. In case of the ceramic heater in the form of a round bar, the distance between the electrode terminals is small and migration is liable to occur at the superficial portion of the heater. In case of the ceramic heater in the form of a rectangular bar, the distance between the electrode terminals can be far larger as compared with that in case of the ceramic heater in the form of a round bar since the electrode terminals can be apart from each other not only in the width direction but in the thickness direction. In this connection, the ceramic heater is formed, similarly to the prior art ceramic heater, from $Al_2O_3$ (alumina) of the purity of more than 90% since alumina is relatively low in cost and excellent in property. However, of 10% or smaller of the impurities of oxides, CaO and/or MgO is desired to be equal to or smaller than 5% with a view to preventing migration of ionized particles since they can be turned into such ionized particles. In the meantime, migration is apt to occur at a superficial portion of the ceramic heater. A long distance between the positive and negative terminals is very effective for improving the migration resisting property. Further, the migration resisting property is largely dependent upon the thickness of the ceramic layer covering the conductive thick film. The more the thickness of the ceramic layer covering the conductive thick-film increases, the more the migration resisting property of the ceramic heater is improved. As shown in FIG. 2, when the ceramic layer covering the conductive thick-film is smaller than 0.25 mm, it is considerably reduced in the durability, that is, the durability of the ceramic layer is considerably reduced due to the migration thereof. Further, when the conductive thick-film is made of cheap tungsten (W), the tungsten forming the conductive thick-film is oxidized by the atmosphere (oxygen) that passes through fine cracks caused in the ceramic layer covering the conductive thick-film due to migration. For this reason, the thickness of the ceramic layer covering the conductive thick-film needs to be equal to or larger than 2 mm and preferably 2.5 mm. In this connection, in case of the ceramic heater in the form of a round bar, the thickness of the ceramic layer converting the conductive thick-film cannot be so thick as desired for the following reason. That is, the diameter of the ceramic core needs to be ten times larger than the thickness of the ceramic green sheets to be wound thereon. This is due to the fact that when the ceramic green sheet is wound on the prefired ceramic core, a crack or cracks are liable to be caused at the outer surface of the ceramic green sheet due to the stretching of the outer surface. To prevent such crack or cracks, the diameter of the ceramic core needs be ten times larger than the thickness of the ceramic green sheet. A screw of the diameter of 18 mm is used for installation of most of current oxygen sensors. When the diameter of the screw is so sized, the maximum diameter of the oxygen ion conductive tube of solid electrolyte is 5.0 mm. Accordingly, the diameter of the heater to be disposed in the oxygen ion conductive tube cannot exceed beyond 4.5 mm. In order to form the ceramic heater in the form of a round bar of the diameter of 4.5 mm, the diameter of the ceramic heater before firing needs to be smaller than 5.4 mm or less by estimating the firing shrinkage at about 20%. Further, bending and warping of the ceramic heater occur at the time of firing. So, by estimating an allowance for the bending and warping, the ceramic heater before firing needs to be 5.2 mm or less (the diameter after firing is 4.3 mm). Thus, even when the thickness of the ceramic green sheet on which the conductive thick-film pattern is printed is set to be 0.24 mm (the green sheet is designed so as to be turned into the ceramic layer of the thickness of 0.2 mm after firing), the thickness of a sheet assembly obtained by laying on the above described ceramic green sheet having printed thereon a conductive thick-film pattern another green sheet, is 0.48 mm. In order to wind the sheet assembly of the thickness of 0.48 mm, the minimum diameter of the ceramic core needs to be 4.8 mm. When this is the case, the heater will be of the minimum diameter of 4.8 mm after firing and therefore cannot be used in the current oxygen sensors. In this connection, in case of the ceramic heater in the form of a rectangular bar or quadrangular prism, the ceramic green sheet is not subjected to such design restrictions, that is, the thickness of the ceramic green sheet can be 0.39 mm, which is 1.5 times or more than 0.25 mm, as described herein later with respect to an embodiment. Thus, the ceramic heater in the form of a rectangular bar is quite effective for attaining an improved migration resisting property. In this connection, since the ceramic heater of this invention is excellent in the migration resisting property, the voltage applied across the electrode terminals can be higher. By this, the performance characteristic at the incipient stage of the oxygen sensor can be improved, that is, the time necessary for activating the oxygen sensor at the time of engine starting can be reduced. By this, it becomes possible to prevent emission of a large amount of unpurified exhaust gases at the time of engine starting.

Figure 3A:
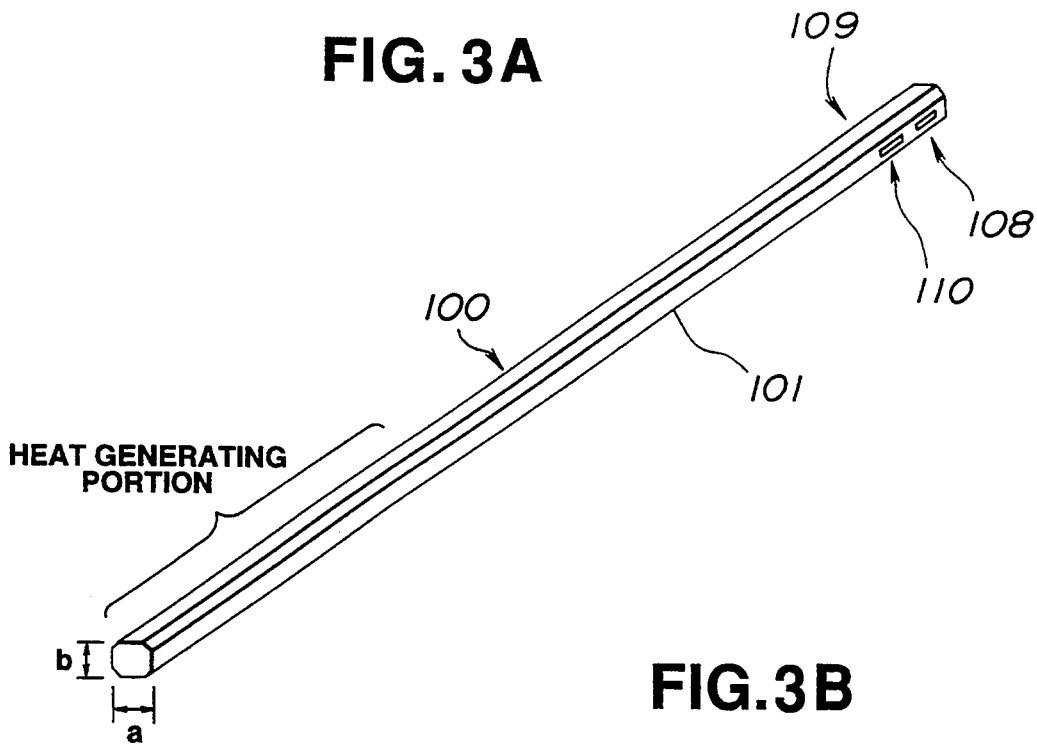
FIG. 3A is a perspective view of a ceramic heater according to an embodiment of the present invention.
Figure 3B:
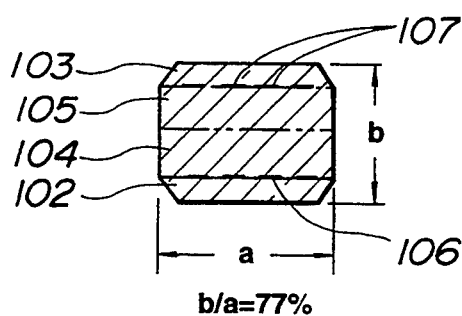
FIG. 3B is a cross sectional view of a heat generating portion of the ceramic heater of FIG. 3A.
Figure 4:
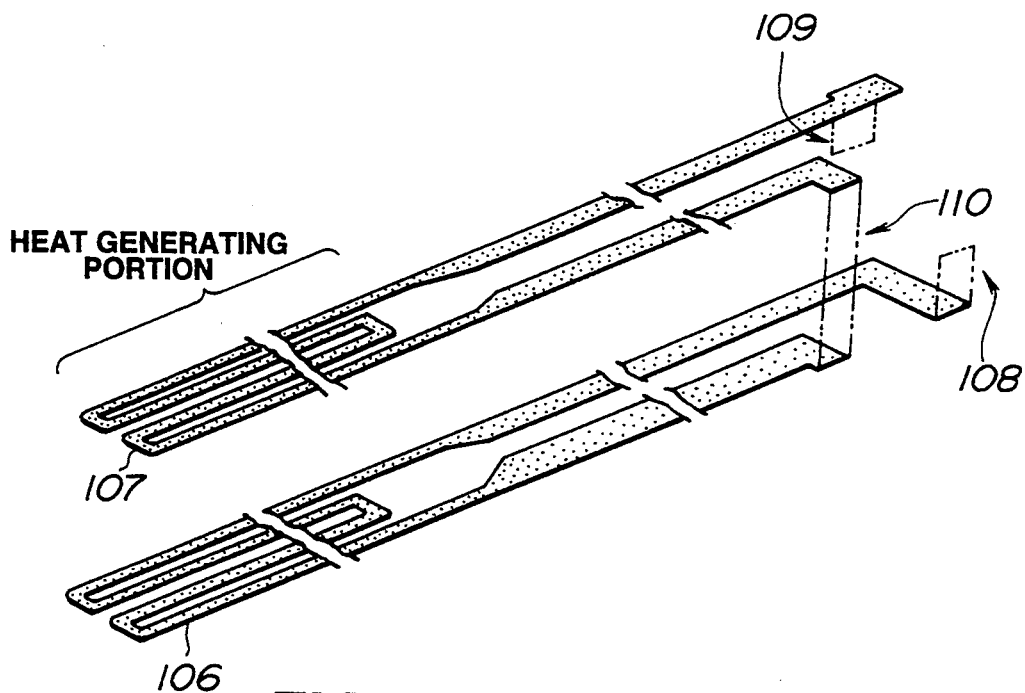
FIG. 4 is an exploded view of metallic thick-films for heat generating resistors embedded in the ceramic heater of FIG. 3A.
Figure 9:
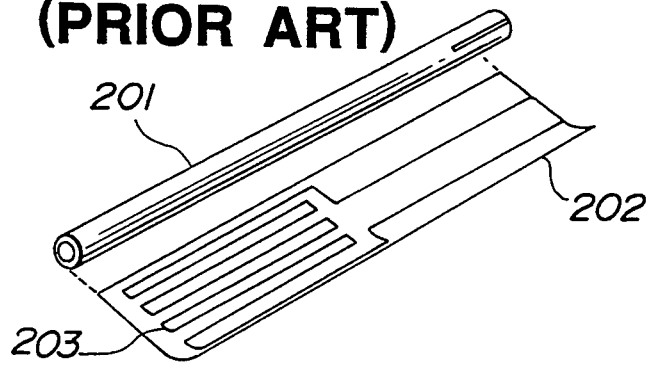
FIGS. 9A and 9B are perspective views of a prior art ceramic heat for use in an oxygen sensor of the type having an oxygen ion conductive tube of solid electrolyte.
Figure 9:
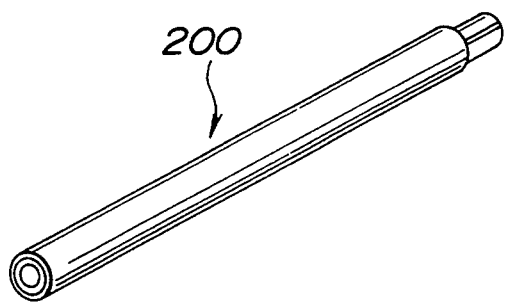
Figures 7A, 7B:
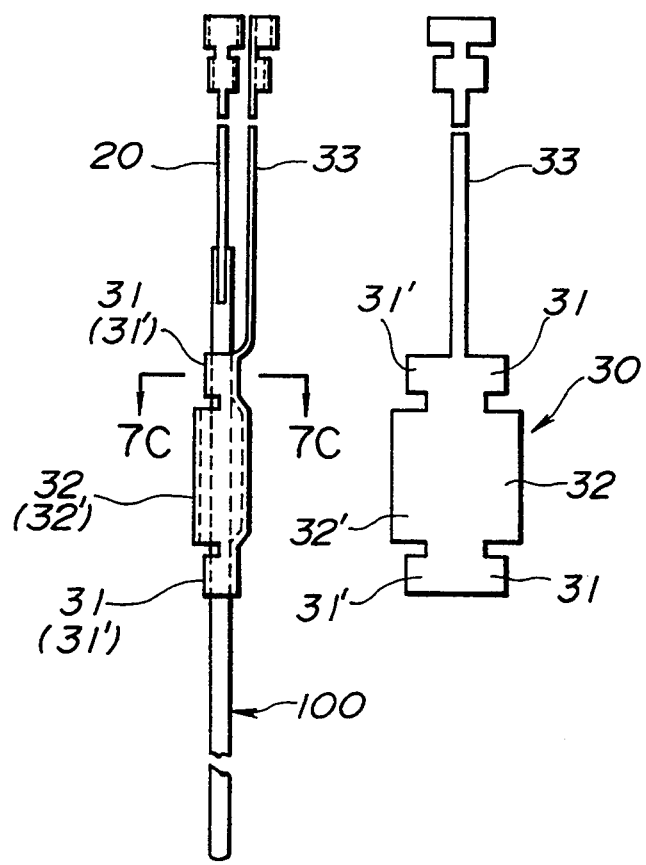
FIG. 7A is a side elevational view of a fixing member used for installing the ceramic heater of FIG. 3A or FIG. 4 in an oxygen sensor.
FIG. 7B is a development view of the fixing member of FIG. 7A.

Referring now to FIGS. 3A–3B and 4, designated by 100 is a ceramic heater for use in an oxygen sensor of the type having an oxygen ion conductive tube of solid electrolyte (designated by 40 in FIG. 7A). The ceramic heater 100 includes a heater main body 101 made of a ceramic material containing 92 wt. % of $Al_2O_3$, 2.0 wt. % of CaO, 1.0 wt. % of MgO, and the remainder of sintering aid as $SiO_2$ and in the form of a straight bar of a rectangular cross section or a quadrangular prism.

In a current oxygen sensor of the above described type, the ion conductive tube of solid electrolyte has, at the inner and outer surfaces thereof, thick-film electrodes of a porous material and is of such a size that the inner diameter of its closed end portion is about 3.3 mm and the length between the bottom and the open end thereof is about 50 mm. In order that the ceramic heater 100 can be suitably used in such an oxygen sensor, it is sized to have the total length of about 64 mm, the thickness "b" of about 2.0 mm and the width "a" of about 2.6 mm. Accordingly, it is determined that b/a=0.77.

Each longitudinal corner or edge is chamfered or beveled in such a manner that the width of the beveled edge is of the width of 0.3 mm. More specifically, the beveled edge is so sized that the ratio of the distance between the center axis of the ceramic heater main body 101 and the beveled edge to the distance between the center axis of the ceramic heater main 101 and each corner is about 1/10. In this connection, it is to be noted that such chamfering is desirable to prevent the edges or corners of the ceramic heater 100 from abutting upon the inner surface of the oxygen ion conductive tube and damaging the same at the time of installation and in use. It is further to be noted that it is desirable to carry out such chamfering in such a manner that the above described ratio is in the range from about 1/20 to ⅓.

As shown in FIGS. 3A–3B and 4, the ceramic heater main body 101 has embedded therein two W(tungsten) thick-films 106 and 107 which extend from an end of the ceramic heater main body 101 to the one third of the total length thereof in a zigzag manner and are arranged in parallel to the side surfaces opposed in the thickness direction. As shown in FIG. 3B which is a cross sectional view of the heat generating portion of the ceramic heater 100, the metallic thick-films 106 and 107 for heat generating resistors are each arranged so as to be interposed between imaginary layers in parallel to the side surfaces of the ceramic heater main body 101 opposed in the thickness direction. That is, the metallic thick-films 106 and 107 for heat generating resistors are interposed between an outer ceramic layer 102 of the thickness of about 0.33 mm and an inner ceramic layer 104 of the thickness of about 0.67 mm and between an inner ceramic layer 105 of the thickness of about 0.67 mm and an outer ceramic layer 103 of the thickness of about 0.33 mm, respectively.

With the ceramic heater 100 structured as above, the metallic thick-films 106 and 107 for heat generating resistors are adapted to generate heat concentrically in the place adjacent to the side surfaces of the heater 100 opposed in the thickness direction thereof.

As shown in FIGS. 3A and 4, the metallic thick-films 106 and 107 for heat generating resistors are interconnected by a wider connecting thick-film 110 which is partially exposed to the outside and also connected to wider terminal or electrode thick-films 108 and 109 which are exposed at end portions to the outside, respectively. A high melting point metal such as W(tungsten), Mo(molybdenum), Re(rhenium), etc. or Pt(platinum), W(tungsten) can suitably be used for forming the metallic thick-films for heat generating resistors. In this embodiment, W(tungsten) is employed to this end.

Each exposed thick-films are applied with Ni-plating. The total resistance of the thick-films 107~110 is 6 ohms, in which the resistance of the metallic thick-films for heat generating resistors 106 and 107 is 4.8 ohms. Accordingly, when the voltage applied across the metallic thick-films 108 and 109 is 14 volts, the power consumption at the metallic thick-films 106 and 107 for heat generating resistors is 8.8 watts at the time of steady state energization.

The ceramic heater 100 is produced as follows.

(1) A mixture of 92 wt. % of $Al_2O_3$ powder, 2 wt. % of CaO, 1 wt. % of MgO and 5 wt. % of $SiO_2$ is prepared and subjected to wet blending for 30 hours to form a slurry.
(2) The slurry is dried at 120° C. by using a drying machine.
(3) A mixture of powders obtained by drying the slurry is screened by means of a screen and then subjected to dry pot mixing for five hours.
(4) Green sheets of the thicknesses of 0.39 mm (0.33 mm after firing), 0.59 mm (0.49 mm after firing), and 0.80 mm (0.67 mm after firing) are prepared by using the mixture of powders screened as above.
(5) A printing ink is prepared by mixing W (tungsten) powder, organic binder and solvent.
(6) Patterns for the metallic thick-films 106 and 107 and of the thickness of about 20 μm are printed on the respective green sheets of the thickness of 0.80 mm by using the ink prepared as above.
(7) The green sheets of the thickness of 0.39 mm and having no metallic thick-film pattern are laid upon the above printed green sheets, respectively and then bonded to each other by application of heat and force to obtain piles.
(8) The piles are laid one upon another in such a manner that the green sheets of the thickness of 0.39 mm are disposed outside and then bonded to each other by application of heat and force to obtain a pile assembly.
(9) The pile assembly is cut and chamfered to size.
(10) Patterns for the exposed connecting thick-film 110 and the exposed terminal thick-films 108 and 109 are printed on the side surfaces of the assembly opposed in the width direction by using the ink prepared as above.
(11) The pile assembly having been cut to size and chamfered is heated at the temperature of 250° C. for 10 hours for removing resinous materials and then fired in an atmosphere of $H_2$ and of the temperature of 1550° C. for two hours.

The ceramic heater 100 is installed in an oxygen sensor in the following manner.

Firstly, as shown in FIG. 7A, terminal elements 20 and 20 are brazed with a silver braze to the exposed terminal thick-films 108 and 109 to which a Ni-plating has been applied. In case of carrying out such brazing, the ceramic heater 100 is placed on a jig made of carbon and the terminal elements 20 and 20 are held in a predetermined positional relation to the exposed terminal thick-films 108 and 109. Then, the ceramic heater 100 and the terminal elements 20 and 20 held as above are passed through a heating furnace so as to be brazed together. In this instance, differing from the prior art ceramic heater in the form of a round, straight bar, the ceramic heater 100 is not easily rolled, so a jig for holding the ceramic heater 100 in place can be quite simple and therefore cheap in cost. Further, by the effect of the chamfered edges or corners, a crack or cracks otherwise caused at the surface of the ceramic heater 100 due to contraction of the brazing material was prevented effectively.

Then, a metallic fixing element 30 is attached to the ceramic heater 100 for securely and elastically attaching the ceramic heater 100 to an oxygen ion conductive tube 40 of solid electrolyte whilst being held in a condition of being deeply inserted into the oxygen ion conductive tube 40 of solid electrolyte. The metallic fixing element 30 is formed from a metallic sheet of the thickness of 0.2 mm which is first cut to such size as shown in FIG. 7B. In this instance, fingers 31 and 31' are formed into a part-cylindrical shape having an opening therebetween so as to be capable of holding the ceramic heater 100 fittingly and elastically. Similarly, fingers 32 and 32' are formed into a part-cylindrical shape so as to be capable of being fixed to the inner wall of the oxygen ion conductive tube 40 of solid electrolyte fittingly and elastically. In this example, the metallic fixing element 30 is adapted to serve as an inner electrode for the oxygen ion conductive tube 40 of solid electrolyte. To this end, the metallic fixing element 30 is integrally formed with an inner electrode terminal 33. The ceramic heater 100 is inserted into the fingers 31 and 32 by elastically expanding the same so as to be securely attached to the metallic fixing element 30. In this instance, as shown in FIG. 7C, by the effect of the chamfered edges or corners, the ceramic heater 100 can contact the fingers 31 and 31' at an increased area, thus making it possible to reduce the stress caused in the ceramic heater 100 at the time of an impact thereto.

Figure 7C:
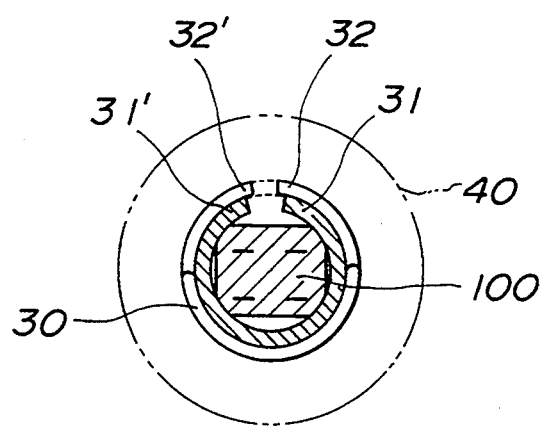
FIG. 7C is a sectional view taken along the line 7C—7C of FIG. 7A.

Under this condition, as shown in FIG. 7C, the fingers 32 and 32' of the metallic fixing element 30 are inserted into the oxygen ion conductive tube of solid electrolyte 40 by being elastically reduced in size, so that the ceramic heater 100 is securely and elastically attached to the oxygen ion conductive tube 40 of solid electrolyte under a condition of being deeply inserted thereinto.

FIGS. 8A and 8B show an oxygen sensor in an assembled condition in which the ceramic heater 100 of this invention is incorporated and fixedly and elastically attached by way of the metallic fixing element 30 to the oxygen ion conductive tube 40 of solid electrolyte with one end closed. The oxygen ion conductive tube 40 of solid electrolyte has porus Pt(platinum) electrode thick-films 41 and 42 secured to the inner and outer surfaces thereof, respectively. The oxygen ion conductive tube 40 of solid electrolyte is attached to a main tubular member 43 by using a leaf packing 44, an inorganic cement 45 and an annular spacer 46. An inner protective tube 47 is also attached at its flange 47a to the main tubular member 43 using the inorganic cement 45 and the annular spacer 46 and by means of a caulking portion 43a of the main tubular member 43. An outer protective tube 48 is placed on the inner protective tube 47 and has disposed therewithin an air permeable or admitting spacer 49 and a silicone rubber seal 50. Lead wires 51 and 52 are connected to the heater terminals 20 and 20, respectively. A lead wire 53 is connected to the inner electrode terminal 33 integral with the metallic fixing element 30. A protector cap 54 formed with gas admitting holes 54a is attached to the main tubular member 43.

At the final stage of the assembly, the inner and outer protective tubes 47 and 48 are fixed to each other by caulking 48a, whilst the silicone rubber seal 50 loosely receiving the lead wires 51, 52 and 53 and the outer protective tube 48 loosely receiving the silicone rubber seal 50 are made to receive them sealingly by caulking 48b. Further, the air serving as a reference oxygen source is introduced into the inside of the oxygen ion conductive tube 40 of solid electrolyte by way of openings between the inner and outer protective tubes 47 and 48, the air permeable spacer 49 and the space between the ceramic heater 100 and the oxygen ion conductive tube of solid electrolyte 40. An output of the oxygen sensor, i.e., the electrical current flowing through the two electrodes 41 and 42 are taken from the lead wire 53 and the main tubular member 43.

Figure 5:
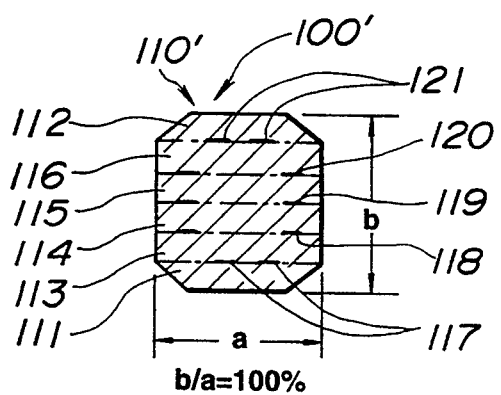
FIG. 5 is a cross sectional view of a heat generating portion of a ceramic heater according to another embodiment of the present invention.
Figure 6:
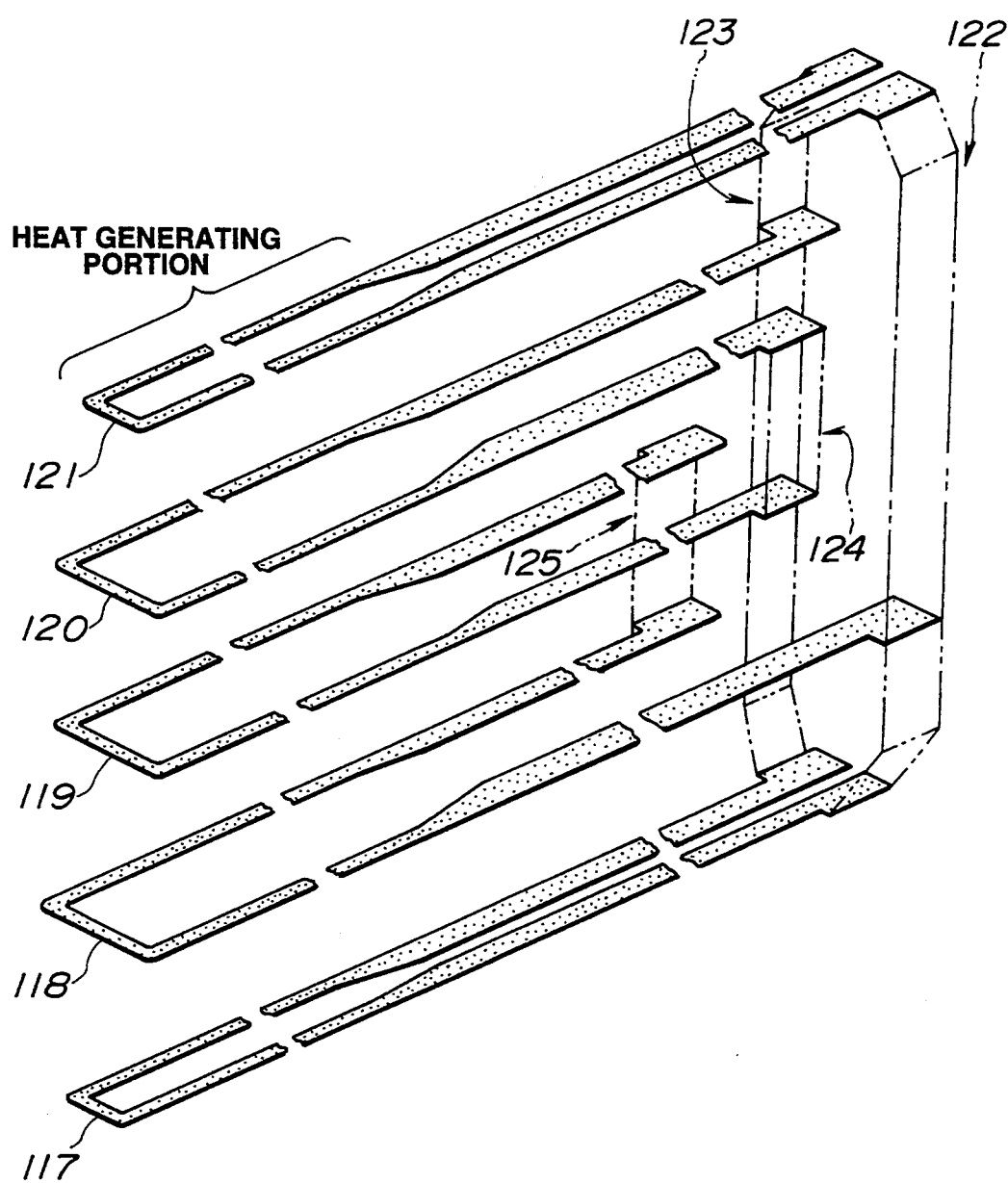
FIG. 6 is an exploded view of metallic thick-films for heat generating resistors embedded in the ceramic heater of FIG. 5.

Referring to FIGS. 5 and 6, a ceramic heater 100' according to a further embodiment is sized so as to have total length of about 64 mm, the width "a" of about 2.6 mm and the thickness "b" of about 2.6 mm. Thus, b/a=1. Each corner is rounded so as to constitute, when viewed in a cross sectional view, part of a circle of the radius of 3.4 mm and drawn with the opposite corner for its center.

In order that a portion of the ceramic heater 100' extending from the front end to the one third of the total length serves as a heat generating portion, the ceramic heater has embedded therewithin thick-films 117, 118, 119, 120 and 121 made of metal as W(tungsten) and arranged in a zig-zag fashion whilst being stacked in the thickness direction to serve as heat generating resistors.

That is, as shown in FIG. 5 which is a cross sectional view of the..heat generating portion, the metallic thick-films for heat generating resistors are interposed between adjacent two imaginary ceramic layers which are parallel to the side surfaces opposed in the thickness direction. Specifically, the metallic thick-film 117 is interposed between one side surface ceramic layer 111 (of the thickness of about 0.33 mm) and an intermediate ceramic layer 113 (of the thickness of about 0.49 mm), the metallic thick-film 118 is interposed between the intermediate ceramic layer 113 and an intermediate ceramic layer 114 (of thickness of about 0.49 mm), the metallic thick-film 119 is interposed between the intermediate layer 114 and an intermediate layer 115 (of the thickness of about 0.49 mm), the metallic thick-film 120 is interposed between the intermediate layer 115 and an intermediate layer 116 (of the thickness of about 0.49 mm), and the metallic thick-film 121 is interposed between the intermediate layer 116 and the other side surface ceramic layer 112 (of the thickness of about 0.33 mm).

The heat generating thick-films in this embodiment are arranged so as to generate heat concentrically at portions adjacent to all of the side surfaces. In the meantime, as shown in FIG. 6, the metallic thick-films 117 and 121 are connected in parallel whilst the metallic thick-films 118, 119 and 120 are connected in series, and moreover all of the metallic thick-films are connected in parallel to the power source so as to generate a smaller amount of heat at or adjacent to the side surfaces of the ceramic heater main body 110' opposed in the width "a" direction and a larger amount of heat at or adjacent to the side surfaces of the ceramic heater main body 110' opposed in the thickness "b" direction.

In FIG. 6, 124 and 125 are exposed connecting thick-films, and 122 and 124 are exposed terminal thick-films. A Ni-plating is applied to the exposed thick-films.

The total input resistance of the metallic thick-films (at the normal temperature) is 3.21 ohms, in which the input resistance of the thick films 117 and 121 adjacent to the side surfaces opposed in the thickness direction is 5 ohms (the resistance of the heat generating portions of the thick films is 2.5 ohms), and the input resistance of the thick films 118, 119 and 120 are 9 ohms (the heat generating portions of the thick films is 5 ohms). When the input voltage is 14 volts, the total power consumption at the normal power supply is 16.5 watts, in which the power consumption of the thick films adjacent to the side surfaces opposed in the thickness direction is 10.6 watts.

This ceramic heater is produced in the manner similar to that of the first embodiment.

The embodiments of the present invention were tested for the strength and durability in the following manner.

Five samples of the first embodiment of FIGS. 3A–3B and 4, and five samples of the second FIG. 5 and 6 were prepared and subjected to the following impact test.

A test oxygen sensor equipped with one of the samples was set on a vibration testing machine and subjected to vibrations of 30G for 30 hours whilst having an end portion heated up to the temperature of 850° C. by using a gas burner. Thereafter, the test oxygen sensor was changed in the set condition, i.e., the test oxygen sensor was rotated 60 degrees and set, and thereafter subjected to vibrations of the same condition for 30 hours, so that the test oxygen sensor was subjected to vibrations of 90 hours in total.

After carrying out the above described vibration test, the test oxygen sensor was disassembled to check any damage of the ceramic heater sample. The result was that there was not caused any breakage or crack in all of the samples and there was not caused any substantial damage in the inner surface of the oxygen ion conductive tube of solid electrolyte.

Further, five samples of each of the embodiments were subjected to the following test of repeated turning on and off of electricity.

The oxygen sensor was attached to a base of a substantially large heat sink and subjected to 50 cycles of test for total 200 hours, in one cycle of test of which the oxygen sensor was supplied with DC current of 17 volts for three successive hours and then cooled for one hour. By the supply of current the temperature of the end portion of the oxygen ion conductive tube of solid electrolyte of the oxygen sensor was heated up to about 510° C. in case of the first embodiment of FIG. 3A–3B and 4 and about 620° C. in case of the embodiment of FIG. 5 and 6.

After the test, the test oxygen sensor was disassembled to check any damage of the ceramic heater. The result was that there was not caused any damage in all of the ceramic heaters of the test oxygen sensors.

A ceramic heater according to a further embodiment is substantially similar to the previous embodiment of FIGS. 3A–3B and 4 except that it is produced by the following processes, that is, a ceramic green body in the form of a bar of a rectangular cross section is firstly prepared, metallic thick-film patterns for heat generating resistors are laid on respective side surfaces of said ceramic green body opposed in the thickness direction, said ceramic green body and said metallic thick-film patterns are cofired to obtain a sintered body formed with metallic thick-films on the side surfaces thereof, and a ceramic powder material is sprayed on said side surfaces of said sintered body to form a fine surface layer covering the ceramic thick-films.

A ceramic heater according to a further embodiment is substantially similar to the previous embodiment of FIGS. 3A–3B and 4 except that its heater main body 101 is made of a ceramic material containing 96 wt. % of $Al_2O_3$, 0.5 wt. % of CaO, 0.5 wt. % of MgO, and 2.0 wt. % of $SiO_2$ and that it is subjected to firing at the temperature of 1600° C. for 2 hours. Samples of this embodiment were prepared and tested for the durability by applying across its electrodes a voltage of DC 16 volts for 300 hours. The result was that a variation of the resistance after the test was an increase of the resistance within 10% of the initial value. In this connection, in case the prior art ceramic heater in the form of a round, straight boar and formed by using the ceramic material of the embodiment of FIGS. 3A–3B and 4, the corresponding increase of the resistance was about 25%. In the meantime, the ceramic material of this embodiment cannot be used to form a ceramic heater in the form of a round bar successfully since this ceramic material is low in viscosity so that a crack or cracks are caused in the ceramic green sheet when wound on a core.

From the foregoing, it will be understood that the ceramic heater of this invention in the form of a rectangular bar and constructed to satisfy a relation of $b/a = 0.75 \sim 1$ can obtain a sufficient transverse rupture strength and thus eliminate the possibility of abutting upon the inner surface of the oxygen ion conductive tube and damaging the same at the time of installation and in use.

It will be further understood that the ceramic heater of this invention can be produced with ease since it does not require a prefired core member and a troublesome work and process for winding a ceramic green sheet thereon. In this connection, a plurality of pile assemblies, from which a ceramic heater of this invention can be obtained by firing, can be formed from a single large pile at one time by a single cutting process using a press or the like, so the ceramic heater of this invention can be produced at a considerably low cost as compared with the prior art ceramic heater.

It will be further understood that the ceramic heater of this invention is superior in migration resisting property and durability to the prior art ceramic heater.

It will be further understood that the ceramic heater of this invention is effective for improving the performance characteristic at the incipient stage of the associated oxygen sensor since it can activate the oxygen sensor at a shorter time at cold starting of the engine since a larger voltage can be applied across the terminal electrodes of the ceramic heater of this invention as compared with the prior art ceramic heater. By this, it becomes possible to prevent emission of a large amount of unpurified exhaust gases at the time of engine starting.

While the present invention has been described and shown as above, it is not for the purpose of limitation. For example, while the ceramic heater main body has been described and shown as being solid, it may be formed with a through hole concentric with its center axis, for introducing the air serving as a reference oxygen source into the solid electrolyte tube.

What is claimed is:

1. A ceramic heater for an oxygen sensor of the type having an oxygen ion conductive tube of solid electrolyte with an end closed, comprising:
   a ceramic heater main body in the form of a quadrangular prism of the width "a" and the thickness "b" and so shaped that the ratio of the thickness "b" to the width "a" is in the range from 0.75 to 1; and
   at least two metallic thick-films for heat generating resistors embedded in said ceramic heater main body in parallel to side surfaces of said ceramic heater main body opposed in the thickness direction.

2. A ceramic heater according to claim 1, wherein said ceramic heater main body is at least partially chamfered at its corners.

3. A ceramic heater according to claim 1, wherein each of said metallic thick-films is covered by a ceramic layer of the thickness of 0.25 mm or larger.

4. A ceramic heater according to claim 1, further comprising a pair of terminal electrodes connected to said metallic thick-films, respectively, said terminal electrodes being located at side surfaces of said ceramic heater main body opposed in the width direction and adjacent to said side surfaces opposed in the thickness direction.

5. A ceramic heater according to claim 1, wherein said ceramic heater main body is formed from a ceramic material containing 96 wt. % of $Al_2O_3$, 0.5 wt. % of CaO, 0.5 wt. % of MgO, and 2.0 wt. % of $SiO_2$.

6. A ceramic heater for use in an oxygen sensor of the type having an oxygen ion conductive tube of solid electrolyte with an end closed by being inserted into the oxygen conductive tube, comprising:

a ceramic heater main body in the form of a bar of a rectangular cross section and so shaped as to satisfy $b/a = 0.75 \sim 1$ where "a" is the width of said ceramic main body and "b" is the thickness of said ceramic main body; and a plurality of metallic thick films for heat generating resistors embedded in said ceramic heater main body in parallel to side surfaces of said ceramic heater main body opposed in the thickness direction;

said metallic thick-films being constructed and arranged so as to generate a less amount of heat at or adjacent to side surfaces of said ceramic heater main body opposed in the width direction and a larger amount of heat at or adjacent to said side surfaces of said ceramic heater main body opposed in the thickness direction.

7. An oxygen sensor comprising:

an oxygen ion conductive tube of solid electrolyte and having an end closed; and a ceramic heater disposed within said oxygen ion conductive tube for heating the same;

said ceramic heater including a ceramic heater main body in the form of a quadrangular prism and so shaped as to satisfy the relation of $b/a = 0.75 \sim 1$ where "a" is the width of said ceramic main body and "b" is the thickness of said ceramic main body, and a plurality of metallic thick-films for heat generating resistors embedded in said ceramic heater main body in parallel to side surfaces of said ceramic heater main body opposed in the thickness direction.

8. An oxygen sensor according to claim 7, wherein said ceramic heater main body is at least partially chamfered at its corners.

9. An oxygen sensor according to claim 7, wherein outermost two of said metallic thick-films located adjacent to said side surfaces opposed in the thickness direction are covered by ceramic layers of the thickness of 0.25 mm or larger, respectively.

10. A ceramic heater according to claim 7, further comprising a pair of terminal electrodes connected said metallic thick-films, respectively, said terminal electrodes being located at side surfaces of said ceramic heater main body opposed in the width direction and adjacent to said side surfaces opposed in the thickness direction.

11. A ceramic heater according to claim 7, wherein said metallic thick-films are constructed and arranged so as to generate a less amount of heat generated at or adjacent to side surfaces of said ceramic heater main body opposed in the width direction and a larger amount of heat at or adjacent to said side surfaces of said ceramic heater main body opposed in the thickness direction is heated.

12. A ceramic heater according to claim 7, wherein said ceramic heater main body is formed from a ceramic material containing 96 wt. of $Al_2O_3$, 0.5 wt. of CaO, 0.5 wt. % of MgO, and 2.0 wt. % of $SiO_2$.

* * * * *